United States Patent [19]

Temple, Jr. et al.

[11] 4,450,160

[45] May 22, 1984

[54] 1,2-DIHYDROPYRIDO[3,4-B]-PYRAZINES AND METHOD AND INTERMEDIATES FOR PREPARING SAME

[75] Inventors: Carroll G. Temple, Jr.; John A. Montgomery; Robert D. Elliott; Glynn P. Wheeler, all of Birmingham, Ala.

[73] Assignee: Southern Research Institute, Birmingham, Ala.

[21] Appl. No.: 354,164

[22] Filed: Mar. 3, 1982

Related U.S. Application Data

[63] Continuation-in-part of Ser. No. 327,928, Dec. 7, 1981, abandoned, which is a continuation-in-part of Ser. No. 247,158, Mar. 24, 1981, abandoned.

[51] Int. Cl.³ .................. C07D 471/04; C07D 213/75
[52] U.S. Cl. .................................... 424/250; 546/308; 564/253; 544/350
[58] Field of Search ........................................ 424/250

[56] References Cited

PUBLICATIONS

Temple, Jr., "Abstract, 28th SE Regional Meeting of ACS" Oct. 27–29, 1976, p. 424.
Elliot et al., J. Org. Chem. 36, 2818 (1971).
Elliot et al., J. Med. Chem. 17, 553 (1974).
Wilson et al., Federation Proceedings, 33, 158 (1974).
Davidse et al., J. Cell. Biol. 72, 174 (1977).
Montomery et al., J. Org. Chem. 29, 734 (1964).
Elliott, J. Org. Chem. 33, 533 (1968).

Primary Examiner—Mark L. Berch
Attorney, Agent, or Firm—Roylance, Abrams, Berdo & Goodman

[57] ABSTRACT 1,2-Dihydropyrido[3,4-b]pyrazines are provided which possess antifungal and anticancer activity. The compounds have the structure:

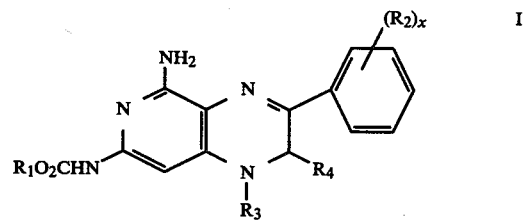

wherein x has a value of 1, 2 or 3; $R_1$ is a lower alkyl group, $R_2$ is a member selected from the group consisting of hydrogen, alkyl radicals having from about one to about 12 carbon atoms, alkenyl radicals having from about two to about 15 carbon atoms, cycloalkyl radicals having from about three to about 20 carbon atoms, aralkyl and alkaryl radicals having from about six to about 20 carbon atoms, a halogen radical, provided that when x has a value of 1 and $R_2$ is in the para position and $R_3$ and $R_4$ are both hydrogen, $R_2$ is not chlorine; a hydroxyl group; an amino group; an alkoxy or aryloxy group; a carboxyl group or an alkylcarboxyl group having from about one to about 10 carbon atoms, an alkylthio group or an arylthio group having from about one to about 20 carbon atoms, a sulfonic acid group or alkyl- or arylsulfonyl group having from about one to about 20 carbon atoms, an alkyl- or arylsulfinyl group having from about one to about 20 carbon atoms, an alkyl- or aryl mono- or diamino group having from about one to about 20 carbon atoms, a hydrocarbyl group, such as defined above, carrying halogen, hydroxyl, amino, alkoxy or aryloxy; and, when taken together with the aromatic ring to which it is attached, a fused ring structure such as naphthyl; and $R_3$ and $R_4$ are either both hydrogen or one is hydrogen and the other is a lower alkyl group.

12 Claims, No Drawings

1,2-DIHYDROPYRIDO[3,4-B]-PYRAZINES AND METHOD AND INTERMEDIATES FOR PREPARING SAME

CROSS-REFERENCES TO RELATED APPLICATIONS

This application is a continuation-in-part of our co-pending application Ser. No. 327,928, filed Dec. 7, 1981, abandoned which is a continuation-in-part of application Ser. No. 247,158, filed Mar. 24, 1981, abandoned.

BACKGROUND OF THE INVENTION

This invention relates to novel 1,2-dihydropyrido[3,4-b]pyrazines, also known as 1-deaza-7,8-dihydropteridines. This invention also relates to a process for making such compounds and to novel intermediates obtained in said process.

The antimitotic chemical agents commonly known as spindle poisons are plant products of which the best known are colchicine, podophyllotoxin, and the vinca alkaloids. [L. Wilson, J. R. Bamburg, S. B. Mizel, L. M. Grisham and K. M. Creswell, *Federation Proceedings*, 33, 158 (1974)]. Two members of the latter, vincristine and vinblastine, are currently used clinically in the treatment of neoplasms. Although these agents produce a number of biochemical actions such as the inhibition of macromolecular synthesis, their primary effect is to prevent mitosis by interfering with the function of microtubules, which results in the accumulation of cells in metaphase. in addition, several benzimidazol-2-yl carbamates have been introduced as fungicides, anthelmintics and antitumoral agents. [L. C. Davidse and W. Flach, *J. Cell Biol.*, 72, 174 (1977)]. These compounds also prevent mitosis and their biological activity can probably be attributed to interference with the formation or functioning of microtubules.

The development of procedures for the preparation of 1-deazapteridines is reported by J. A. Montgomery and N. F. Wood, *J. Org. Chem.*, 29, 734 (1964); R. D. Elliott, C. Temple, Jr. and J. A. Montgomery, *J. Org. Chem.*, 33, 533 (1968); R. D. Elliott, C. Temple, Jr., J. L. Frye and J. A. Montgomery, *J. Org. Chem.*, 36, 2818 (1971); and R. D. Elliott, C. Temple, Jr. and J. A. Montgomery, *J. Med. Chem.*, 17, 553 (1974). These references disclose the preparation and use of various 1,2-dihydro[3,4-b]pyrazine derivatives. Thus, the 1964 *J. Org. Chem.* reference discloses the compounds:

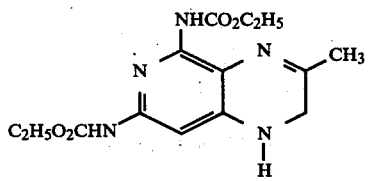

and

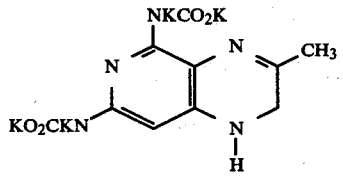

the 1968 *J. Org. Chem.* reference discloses the compound:

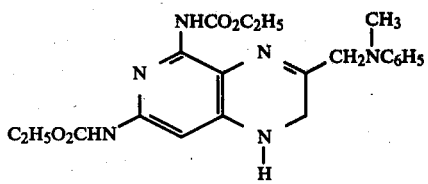

The 1971 *J. Org. Chem.* reference discloses the compounds:

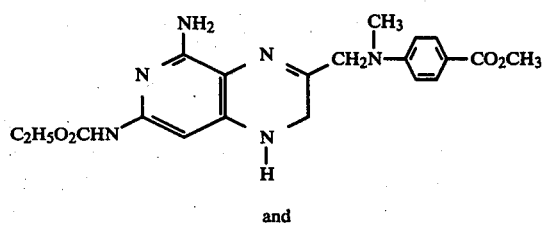

and

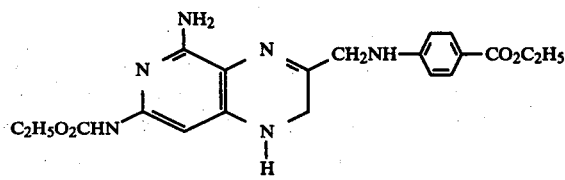

The *J. Med. Chem.* reference discloses that a dihydro-1-deazapteridine precursor of 1-deazamethotrexate showed activity against leukemia L1210 in mice. An abstract presented at the 28th Southeast Regional Meeting of the American Chemical Society in Gatlinburg, Tenn., Oct. 27–29, 1976 discloses that the compound

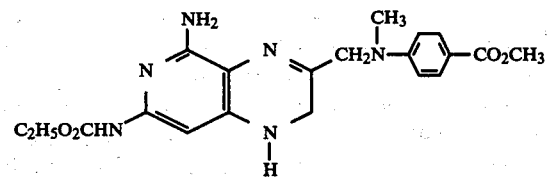

showed cytotoxicity in the KB cell culture screen and activity against leukemia L1210 in mice.

SUMMARY OF THE INVENTION

It has now been found that certain 1,2-dihydropyrido[3,4-b]pyrazines which are not disclosed in any of the references discussed in the preceding section possess antifungal and anticancer activity. The compounds of this invention have the structure:

wherein x has a value of 1, 2 or 3; $R_1$ is a lower alkyl group, e.g., an alkyl group containing up to six carbon atoms such as methyl, ethyl, propyl, butyl, etc.; $R_2$ is a member selected from the group consisting of hydrogen, alkyl radicals having from about one to about 12 carbon atoms, preferably from about one to about 6 carbon atoms; alkenyl radicals having from about two to about 15 carbon atoms, preferably from about two to about 10 carbon atoms; cycloalkyl radicals having from about three to about 20 carbon atoms, preferably from about three to about 15 carbon atoms; aralkyl and alkaryl radicals having from about six to about 20 carbon atoms, preferably from about six to about 15 carbon atoms; a halogen radical, e.g., chlorine, fluorine, bromine and iodine, provided that when x has a value of 1 and $R_2$ is in the para position and $R_3$ and $R_4$ are both hydrogen, $R_2$ is not chlorine; a hydroxyl group; an amino group; an alkoxy or aryloxy group; a carboxyl group or an alkylcarboxyl group having from about one to about 10 carbon atoms, preferably from about one to about 5 carbon atoms; an alkylthio group or an arylthio group having from about one to about 20 carbon atoms, preferably from about one to about 15 carbon atoms; a sulfonic acid group or alkyl- or arylsulfonyl group having from about one to about 20 carbon atoms, preferably from about one to about 15 carbon atoms; an alkyl- or arylsulfinyl group having from about one to about 20 carbon atoms, preferably from about one to about 15 carbon atoms; an alkyl- or aryl mono- or diamino group having from about one to about 20 carbon atoms, preferably from about one to about 15 carbon atoms; a hydrocarbyl group, such as defined above, carrying halogen, hydroxyl, amino, alkoxy or aryloxy; and, when taken together with the aromatic ring to which it is attached, a fused ring structure such as naphthyl; and $R_3$ and $R_4$ are either both hydrogen or one is hydrogen and the other is a lower alkyl group.

Compounds of Formula I wherein $R_3$ is hydrogen may be prepared by aminating a lower alkyl ester of 6-amino-4-chloro-5-nitropyridin-2-ylcarbamate having the structure:

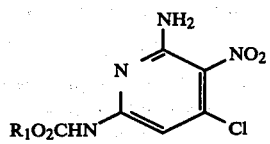

with the oxime of an alpha-amino ketone having the structure:

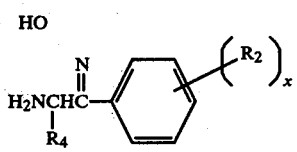

to give a lower alkyl ester of a 6-amino-5-nitro-4-[(2-oxoethyl)amino]pyridin-2-ylcarbamate oxime having the structure:

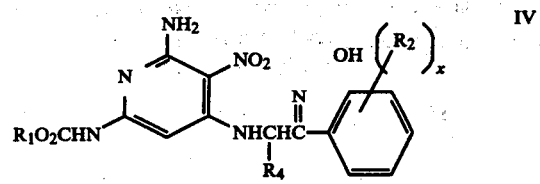

wherein $R_1$, $R_2$, $R_4$ and x are the same as previously defined, further provided that $R_2$ may be a nitro group. The compound of Formula IV is hydrolyzed, e.g., by acid hydrolysis to give the corresponding ketone having the formula:

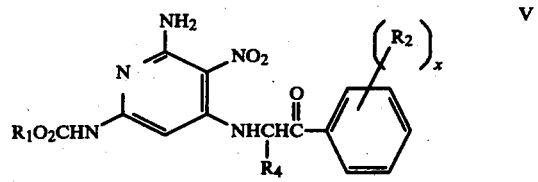

wherein $R_1$, $R_2$, $R_4$ and x are the same as previously defined, further provided that $R_2$ may be a nitro group. The compound of Formula V is converted to the compound of Formula I by catalytic hydrogenation. An intermediate product formed during hydrogenation has the formula:

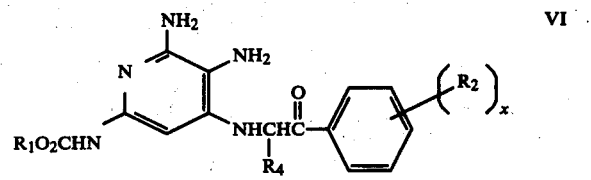

wherein $R_1$, $R_2$, $R_4$ and x are the same as previously defined.

Compounds of Formula I wherein $R_4$ is hydrogen may be prepared by aminating the compound of Formula II with an alpha-amino alcohol having the structure:

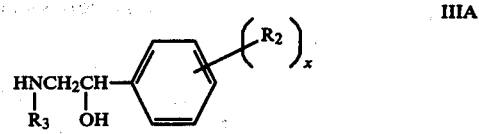

to give a compound having the structure:

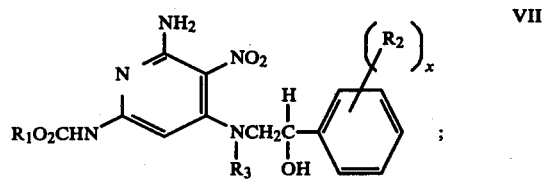

which is oxidized to give a ketone having the structure:

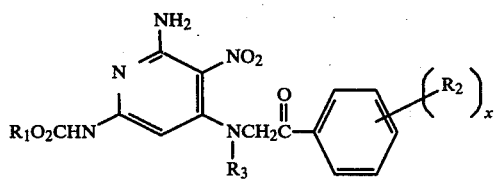

VA wherein $R_1$, $R_2$, $R_3$ and x are the same as previously defined, further provided that $R_2$ may be a nitro group. The compound of Formula VA is converted to a compound of Formula I by catalytic hydrogenation.

DETAILED DESCRIPTION OF THE INVENTION

A preferred lower alkyl ester of 6-amino-4-chloro-5-nitropyridin-2-ylcarbamate is the ethyl ester, i.e., ethyl 6-amino-4-chloro-5-nitropyridin-2-ylcarbamate. This compound is prepared according to the procedure described by R. D. Elliott, C. Temple, Jr. and and J. A. Montgomery, J. Org. Chem., 31, 1890 (1966).

Oximes of alpha-amino ketones, i.e., compounds of Formula III, may be prepared by known prior art procedures. Thus, they can be prepared by reacting the corresponding alpha-bromoacetophenone with hexamethylenetetramine to give the corresponding ammonium salt which is hydrolyzed by ethanolic hydrochloric acid to give the corresponding alpha-aminoacetophenone hydrochloride [L. M. Long and H. D. Troutman, J. Amer. Chem. Soc., 71, 2473 (1949); and A. B. Sen and D. D. Mukerji, J. Indian Chem. Soc., 28, 401 (1951)]. The condensation of these alpha-amino ketones with hydroxylamine hydrochloride in a refluxing mixture of pyridine and ethanol gives the oxime derivatives [R. D. Elliott, C. Temple, Jr. and J. A. Montgomery, J. Org. Chem., 35, 1676 (1970)].

The compounds of Formula III can also be prepared by alkylation of phthalimide with the corresponding alpha-bromoacetophenone, treatment of the alpha-(phthalimido)-acetophenone product [G. C. Schweiker, Dissertation Abstracts, 21, 464 (1953)] with hydroxylamine, and removal of the phthaloyl protecting group from the resulting oxime with hydrazine [R. D. Elliott, C. Temple, Jr. and J. A. Montgomery, J. Org. Chem., 35, 1676 (1970)].

Examples of these two procedures for the preparation of compounds of Formula III follow:

Method I. α-Amino-2,4-dichloroacetophenone Oxime

α,2,4-Trichloroacetophenone (15 g, 67 mmol) was added with stirring to a suspension of potassium phthalimide (16 g, 86 mmol) in N,N-dimethylformamide (68 ml) at 5° C. After 5 minutes, the resulting solution was allowed to warm to room temperature followed by heating at 50° C. for 15 minutes. The solution was mixed successively with CHCl$_3$ (103 ml) and H$_2$O (341 ml), and the H$_2$O phase was separated and extracted with additional CHCl$_3$ (3×46 ml). The combined CHCl$_3$ extracts were washed with 2% NaOH (57 ml) and H$_2$O (57 ml), and evaporated to a small volume in vacuo (40° C.) The residue was diluted with cold H$_2$O (225 ml), and the mixture was chilled to deposit a semisolid, which was separated by decantation. The residue was washed with C$_2$H$_5$OH and (C$_2$H$_5$)$_2$O and dried to give the phenacyl phthalimide: yield, 9.2 g. A solution of this solid (28 mmol) and hydroxylamine hydrochloride (2.9 g, 41 mmol) in a mixture of pyridine (28 ml) and C$_2$H$_5$OH (117 ml) was stirred at reflux for 1.5 hours. The solvent was evaporated in vacuo, and the resulting oily ketone oxime was washed with H$_2$O: mass spectrum, m/e 348 (M+). A solution of the oxime in ethanol (332 ml) at 70° C. was treated dropwise during 20 minutes with a solution of 95% hydrazine (2.0 g) in ethanol (25 ml). The resulting solution was heated at 40° C. for 22 hours, and the cooled reaction mixture was treated with 1 N HCl (30 ml). After stirring in an ice bath for 1 hour, the precipitated phthalhydrazide was removed by filtration and washed with 1:1 ethanol-water (36 ml). The combined filtrate and wash was evaporated to dryness in vacuo (40° C.), the residue was extracted with warm water (120 ml), and the filtrate was treated with concentrated NH$_4$OH (2 ml) to deposit the product: yield, 3.2 g.

Method II. α-Amino-p-nitroacetophenone Oxime

A solution of α-bromo-p-nitroacetophenone (20 g., 82 mmol) and hexamethylenetetramine (12 g., 86 mmol) in chloroform (300 ml) was stirred at room temperature for 24 hours. The quaternary salt (34 g.) was collected by filtration and stirred in a mixture of ethanol (175 ml) and concentrated hydrochloric acid (55 ml) for 19 hours to give the hydrochloride salt: yield, 9.0 g. A suspension of this product and hydroxylamine hydrochloride (10 g.) in 1:1 ethanol-pyridine (135 ml) was refluxed with stirring for two hours, evaporated to dryness in vacuo, and the resulting residue was dissolved in water and treated with 50% sodium hydroxide to deposit the product: yield, 3.2 g.

The oximes set forth in Table I were prepared by Method I or Method II, as indicated in Table I. The first column of Table I sets forth the structure of the group

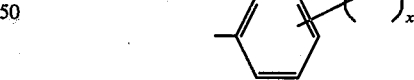

in Formula III. Known compounds are referenced with superscript letters in Table I.

TABLE I

α-Aminoketone Oximes

| Compound[a] | Method | Yield, %[b] | M.p. °C. | Formula | Calcd, % C | H | N | Found, % C | H | N |
|---|---|---|---|---|---|---|---|---|---|---|
| C$_6$H$_5$[c] | II | 40 | 96–110 | C$_8$H$_{10}$N$_2$O | 63.98 | 6.71 | 18.65 | 63.64 | 6.85 | 18.58 |
| 4-CH$_3$C$_6$H$_4$[d] | I | 34 | 127–29 | C$_9$H$_{12}$N$_2$O.0.13C$_2$H$_6$O | 65.34 | 7.57 | 16.46 | 65.18 | 7.48 | 16.42 |
| 2,4-(CH$_3$)$_2$C$_6$H$_3$ | I | 64 | e | C$_{10}$H$_{14}$N$_2$O[f] | | | | | | |
| 3,4-(CH$_3$)$_2$C$_6$H$_3$ | I | 34 | 115–8 | C$_{10}$H$_{14}$N$_2$O.0.64HCl | 59.59 | 7.31 | 13.90 | 59.51 | 7.14 | 14.05 |
| 4-FC$_6$H$_4$ | II | 70 | 142–3 | C$_8$H$_9$FN$_2$O[h] | | | | | | |
| 2,4-(Cl)$_2$C$_6$H$_3$ | I | 22 | 115–20[i] | C$_8$H$_8$Cl$_2$N$_2$O.0.17H$_2$O | 43.25 | 3.78 | 12.60 | 43.30 | 3.84 | 12.52 |
| 3,4-(Cl)$_2$C$_6$H$_3$ | I | 91 | 123–7 | C$_8$H$_8$Cl$_2$N$_2$O | 43.86 | 3.68 | 12.79 | 43.80 | 3.82 | 12.91 |

TABLE I-continued

α-Aminoketone Oximes

| Compound[a] | Method | Yield, %[b] | M.p. °C. | Formula | Calcd, % C | H | N | Found, % C | H | N |
|---|---|---|---|---|---|---|---|---|---|---|
| 3-CH$_3$OC$_6$H$_4$ | I | 77 | e | C$_9$H$_{12}$N$_2$O$_2$ | | | | | | |
| 4-CH$_3$OC$_6$H$_4$[d] | II | 6 | 137-9 | C$_9$H$_{12}$N$_2$O.HCl.0.31H$_2$O | 48.64 | 6.18 | 12.60 | 48.55 | 6.02 | 12.37 |
| 3,4,5-(CH$_3$O)$_3$C$_6$H$_2$ | I | 70 | 134-7 | C$_{11}$H$_{16}$N$_2$O$_4$.0.16C$_2$H$_6$O | 54.90 | 6.90 | 11.31 | 54.84 | 7.10 | 11.29 |
| 4-O$_2$NC$_6$H$_4$[k] | II | 19 | 124-5 | C$_8$H$_9$N$_3$O$_3$.0.28HCl | 46.78 | 4.55 | 20.45 | 47.10 | 4.41 | 20.12 |
| 4-CF$_3$C$_6$H$_4$[l] | I | 31 | 129-30 | C$_9$H$_9$F$_3$N$_2$O | 49.54 | 4.16 | 12.84 | 49.35 | 4.13 | 12.83 |
| 2-C$_{10}$H$_7$ | II | 98 | 125-30 | C$_{12}$H$_{12}$N$_2$O[m] | | | | | | |
| C$_6$H$_5$, R$_4$ = CH$_3$[c] | II | 68 | e | C$_9$H$_{12}$N$_2$O[n] | | | | | | |

[a] R$_4$ = H unless otherwise specified;
[b] Overall yield;
[c] Gnichtel, H., Chem. Ber. 1965, 98, 567;
[d] Gnichtel, H., Chem. Ber. 1970, 103, 3442;
[e] Oil;
[f] m/e 178 (M$^+$);
[g] phthalimide intermediate, Chen, S. -S., Jonsson, S., and Semeniuk, F.T., J. Pharm. Sci. 1962, 51, 108;
[h] m/e 168 (M$^+$);
[i] Presoftening 76-81° C.;
[j] m/e 180 (M$^+$);
[k] Aminoketone intermediate, Long, L.M. and Troutman, H.D., J. Amer. Chem. Soc. 1949, 71, 2473,
[l] Phthalimide intermediate, Schweiker, G.C., Dissertation Abstracts 1953, 21, 464;
[m] m/e 200 (M$^+$);
[n] m/e 164 (M$^+$).

The alpha-amino alcohol of Formula IIIA wherein R$_2$ is hydrogen and R$_3$ is CH$_3$ was prepared in accordance with the procedure described by S. P. McManus, C. A. Larson and R. A. Hearn, Synthetic Commun., 3, 177 (1973). The product, having the empirical formula C$_9$H$_{13}$NO, m/e 151 (M$^+$), and a melting point of 75°-77° C., was obtained in a 52% overall yield.

A compound of Formula II is animated with a compound of Formula III under nitrogen in refluxing ethanol containing triethylamine as an acid acceptor to give a compound of Formula IV. An example of this procedure follows:

EXAMPLE 1

Ethyl 6-Amino-5-nitro-4-[(2-oxo-2-phenylethyl)amino]pyridin-2-ylcarbamate oxime (IV: R$_1$=C$_2$H$_5$; R$_2$=H; R$_4$=H)

A solution of ethyl 6-amino-4-chloro-5-nitropyridin-2-ylcarbamate (14.0 g., 53.8 mmoles), alpha-aminoacetophenone oxime (8.07 g., 53.8 mmoles), and triethylamine (5.43 g., 53.8 mmoles) in ethyl alcohol (300 ml.) was refluxed under N$_2$ with stirring for eight hours. The solid that deposited from the cooled reaction mixture was cooled by filtration and dried in vacuo over P$_2$O$_5$: yield 10.4 g. The properties are set forth in Table II.

Additional compounds were prepared similarly wherein the alpha-aminoacetophenone oxime was replaced with substituted alpha-aminoacetophenone oximes. The properties of these compounds are set forth in Table II. The first column of Table II sets forth the structure of the group:

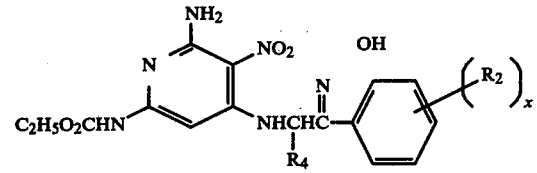

in the starting alpha-aminoacetophenone oxime, and in the final product, the formula for which appears in Table II.

TABLE II

Ethyl 6-Amino-5-nitro-4-[(2-oxo-2-phenylethyl)amino]pyridin-2-ylcarbamate oximes

| Compound[a] | Reaction Time, Hours | Yield, % | M.p. °C. | Formula | Calcd, % C | H | N | Found, % C | H | N |
|---|---|---|---|---|---|---|---|---|---|---|
| C$_6$H$_5$ | 8 | 52 | 245-6 dec | C$_{16}$H$_{18}$N$_6$O$_5$ | 51.33 | 4.85 | 22.45 | 51.23 | 5.03 | 22.38 |
| 4-CH$_3$C$_6$H$_4$ | 2 | 87 | 234-5 dec | C$_{17}$H$_{20}$N$_6$O$_5$.0.22HCl | 51.50 | 5.14 | 21.20 | 51.59 | 5.28 | 21.23 |
| 2,4-(CH$_3$)$_2$C$_6$H$_3$ | 2 | 18 | 198-100 | C$_{18}$H$_{22}$N$_6$O$_5$ | 53.73 | 5.51 | 20.88 | 53.94 | 5.81 | 20.97 |
| 3,4-(CH$_3$)$_2$C$_6$H$_3$ | 1.5 | 82 | 236-7 dec | C$_{18}$H$_{22}$N$_6$O$_5$.0.25H$_2$O | 53.13 | 5.57 | 20.65 | 52.98 | 5.71 | 20.93 |
| 4-FC$_6$H$_4$ | 2 | 86 | 240-2 | C$_{16}$H$_{17}$FN$_6$O$_5$.0.13HCl | 48.40 | 4.35 | 21.16 | 48.30 | 4.19 | 21.17 |
| 2,4-(Cl)$_2$C$_6$H$_3$ | 2.5 | 45 | 177-9 dec | C$_{16}$H$_{16}$Cl$_2$N$_6$O$_5$ | 43.35 | 3.64 | 18.96 | 43.71 | 3.89 | 18.92 |
| 3,4-(Cl)$_2$C$_6$H$_3$ | 1.5 | 64 | 214-6 | C$_{16}$H$_{16}$Cl$_2$N$_6$O$_3$.0.54C$_2$H$_6$O | 43.78 | 4.10 | 18.03 | 43.66 | 3.59 | 18.03 |
| 3-CH$_3$OC$_6$H$_4$ | 3 | 56 | 223-7 dec | C$_{17}$H$_{20}$N$_6$O$_6$ | 50.49 | 4.99 | 20.78 | 50.26 | 5.03 | 21.05 |
| 4-CH$_3$OC$_6$H$_4$ | 4 | 55 | 218-9 dec | C$_{17}$H$_{20}$N$_6$O$_6$.0.12HCl | 49.94 | 4.97 | 20.56 | 49.92 | 4.91 | 20.57 |
| 3,4,5-(CH$_3$O)$_3$C$_6$H$_2$ | 1 | 37 | 205-8 dec | C$_{19}$H$_{24}$N$_6$O$_8$.0.2HCl | 48.37 | 5.17 | 17.82 | 48.38 | 5.48 | 17.86 |

TABLE II-continued

Ethyl 6-Amino-5-nitro-4-[(2-oxo-2-phenyl-ethyl)amino]pyridin-2-ylcarbamate oximes

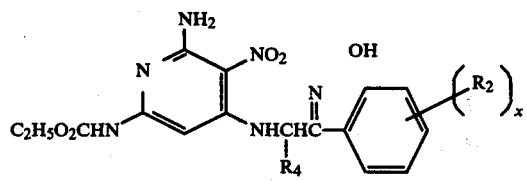

| Compound[a] | Reaction Time, Hours | Yield, % | M.p. °C. | Formula | Calcd, % C | Calcd, % H | Calcd, % N | Found, % C | Found, % H | Found, % N |
|---|---|---|---|---|---|---|---|---|---|---|
| 4-$O_2NC_6H_4$ | 2 | 44 | 207-8 dec | $C_{16}H_{17}N_7O_7$ | 45.83 | 4.08 | 23.38 | 46.02 | 4.23 | 23.33 |
| 4-$CF_3C_6H_4$ | 2 | 47 | 224-5 dec | $C_{17}H_{17}F_3N_6O_5$ | 46.16 | 3.87 | 19.00 | 45.78 | 3.85 | 18.81 |
| 2-$C_{10}H_7$ | 1 | 49 | 216-9 | $C_{20}H_{20}N_6O_5$[b] | | | | | | |
| $C_6H_5$, $R_4$ = $CH_3$ | 2 | 31 | 176-8 | $C_{17}H_{20}N_6O_5$·0.1HCl | 52.08 | 5.17 | 21.43 | 51.96 | 5.36 | 21.37 |

[a] $R_4$ = H unless otherwise specified;
[b] m/e 424 (M+).

Treatment of a compound of Formula IV with a 1:1 mixture of 1 N hydrochloric acid and dioxane at 60° C. hydrolyzes the oxime function to give a compound of Formula V. An example of this procedure follows:

EXAMPLE 2

Ethyl 6-Amino-5-nitro-4-[(2-oxo-2-phenylethyl)amino]pyridin-2-ylcarbamate dioxanate (V: $R_1$=$C_2H_5$; $R_2$=H; $R_4$=H)

A solution of ethyl 6-amino-5-nitro-4-[(2-oxo-2-phenylethyl)amino]pyridin-2-ylcarbamate oxime (4.72 g., 12.6 mmoles) in a 1:1 mixture of 1 N HCl-dioxane (170 ml.) was heated with stirring at 60° C. for two hours. The yellow solid that deposited from the chilled solution was collected by filtration and recrystallized from a 1:1 mixture of $H_2O$-dioxane (1 L.): yield, 3.13 g.

Additional compounds were prepared similarly wherein the oxime starting material was replaced with substituted ethyl 6-amino-5-nitro-4-[(2-oxo-2-phenylethyl)amino]pyridin-2-ylcarbamate oximes. The properties of these compounds are set forth in Table III. The first column of Table III sets forth the structure of the group

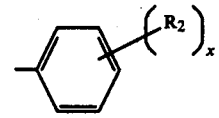

in the starting oxime, the formula for which appears in Table II, and in the final product, the formula for which appears in Table III.

TABLE III

Ethyl 6-Amino-5-nitro-4-[(2-oxo-2-phenyl-ethyl)amino]pyridin-2-ylcarbamates

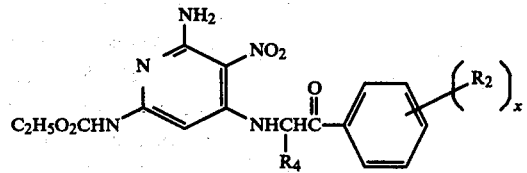

| Compound[a] | Reaction Time, Hours | Yield, % | M.p. °C. | Formula | Calcd, % C | Calcd, % H | Calcd, % N | Found, % C | Found, % H | Found, % N |
|---|---|---|---|---|---|---|---|---|---|---|
| $C_6H_5$ | 2 | 59 | 177-8 | $C_{16}H_{17}N_5O_5$·0.66$C_4H_8O_2$·0.16$H_2O$ | 53.26 | 5.36 | 16.62 | 53.18 | 5.40 | 16.63 |
| 4-$CH_3C_6H_4$ | 3 | 73 | 184-5 | $C_{17}H_{19}N_5O_5$ | 54.69 | 5.13 | 18.76 | 59.26 | 5.13 | 18.76 |
| 3,4-$(CH_3)_2C_6H_3$ | 4 | 80 | 196-7 dec | $C_{18}H_{21}N_5O_5$ | 55.81 | 5.46 | 18.08 | 55.79 | 5.67 | 18.09 |
| 4-$FC_6H_4$ | 24 | 48 | 204-5 | $C_{16}H_{16}FN_5O_5$ | 50.93 | 4.27 | 18.56 | 51.05 | 4.45 | 18.63 |
| 3,4-$(Cl)_2C_6H_3$ | 6 | 69 | 191-2 | $C_{16}H_{15}Cl_2N_5O_5$·0.25$C_4H_8O_2$ | 45.45 | 3.81 | 15.59 | 45.57 | 3.60 | 15.65 |
| 3-$CH_3OC_6H_4$ | 5 | 81 | >171-2 dec | $C_{17}H_{19}N_5O_6$·0.8$H_2O$ | 50.57 | 5.14 | 17.34 | 50.26 | 4.89 | 17.55 |
| 4-$CH_3OC_6H_4$ | 20 | 53 | 194 dec | $C_{17}H_{19}N_5O_6$ | 52.44 | 4.92 | 17.99 | 52.41 | 5.02 | 17.63 |
| 3,4,5-$(CH_3O)_3C_6H_2$ | 2.5 | 80 | 192-3 dec | $C_{19}H_{23}N_5O_8$·2.2$H_2O$·0.1$C_4H_8O_2$ | 46.80 | 5.71 | 14.06 | 46.78 | 5.53 | 14.08 |
| 4-$O_2NC_6H_4$ | 24 | 65 | 204-5 dec | $C_{16}H_{16}N_6O_7$·HCl·$H_2O$ | 41.88 | 4.17 | 18.32 | 41.75 | 4.45 | 18.05 |
| 4-$CF_3C_6H_4$ | 2 | 31 | 166.5-7.5 | $C_{17}H_{16}F_3N_5O_5$·0.75$C_4H_8O_2$ | 48.38 | 5.08 | 14.11 | 48.35 | 4.64 | 14.07 |
| 2-$C_{10}H_7$ | 4 | 66 | 198-9 | $C_{20}H_{19}N_5O_5$·0.1$C_4H_8O_2$ | 58.59 | 4.77 | 16.74 | 58.74 | 4.89 | 16.65 |
| $C_6H_5$, $R_4$ = $CH_3$ | 7 | 98 | 168-74 | $C_{17}H_{19}N_5O_5$·$H_2O$·0.33$C_4H_8O_2$ | 52.33 | 5.67 | 16.66 | 52.20 | 5.62 | 16.60 |

[a] $R_4$ = H unless otherwise specified.

The properties of the compound thus obtained are set forth in Table III.

Amination of the compound of Formula II with a compound of Formula IIIA in refluxing ethanol containing triethylamine as an acid acceptor gives a compound of Formula VII. Oxidation of a compound of Formula VII gives a ketone of Formula VA. An example of this procedure follows:

EXAMPLE 3

A. Ethyl 6-Amino-4-[(N-(2-hydroxy-2-phenylethyl-N-methyl-)amino]5-nitropyridin-2-ylcarbamate (VII: $R_1=C_2H_5$; $R_2=H$; $R_3=CH_3$)

A solution of ethyl 6-amino-4-chloro-5-nitropyridin-2-ylcarbamate (3.40 g., 13.1 mmol), 2-(methylamino)-1-phenylethanol (2.17 g., 14.4 mmol), and triethylamine (1.32 g., 13.1 mmol) in ethanol (75 ml) was refluxed with protection by a drying tube for 2 hours and evaporated to dryness in vacuo. The residue was stirred with 1 N HCl for 1 hour followed by neutralization (pH 7) with 1 N NaOH. The product was collected by filtration and used without further purification: yield, 4.81 g.; m.p. 108°–10° C. Formula: $C_{17}H_{21}N_5O_5$ m/e 375 (M+).

B. Ethyl 6-Amino-4-[(N-methyl-N-2-oxo-2-phenylethyl)amino]-5-nitro-pyridin-2-ylcarbamate (VA: $R_1=C_2H_5$; $R_2=H$; $R_3=CH_3$)

To a solution of pyridine (8.70 g., 110 mmol) in $CH_2Cl_2$ (131 ml), protected with a drying tube, chromium (VI) oxide (5.52 g., 55.2 mmol) was added with stirring. After 15 minutes, a solution of ethyl 6-amino-4-[[(N-(2-hydroxy-2-phenylethyl)-N-methyl]amino]-5-nitropyridin-2-ylcarbamate (3.45 g., 9.20 mmol) in $CH_2Cl_2$ (35 ml.) was added. After an additional 20 minutes, the residue was separated by decantation and washed with $(C_2H_5)_2O$ (242 ml). The combined decant and wash was evaporated to dryness, the residue was dissolved in $(C_2H_5)_2O$ (1700 ml.), and the solution was washed with aqueous 5% $NaHCO_3$ (200 ml), $H_2O$ (200 ml) and saturated NaCl solution (200 ml.). Concentration of the $(C_2H_5)_2O$ solution to a small volume followed by cooling in an ice bath gave the product: yield, 1.99 g.; m.p. 139°–40° C.; Anal. Calcd. for $C_{17}H_{19}N_5O_5$: C, 54.69; H, 5.13; N, 18.76. Found: C, 54.88; H, 5.49; N, 18.50.

The catalytic hydrogenation of a compound of Formula V or VA with a three-fold amount of Raney nickel in a large volume of ethanol (i.e., more than one liter per gram) at atmospheric pressure at room temperature or with intermittent warming (e.g., to no higher than 60° C.) with a water bath gives the intermediate compound of Formula VI which is cyclized in situ with the elimination of water to give a compound of Formula I. Such reaction is shown in Example 4. The compounds of Formula I can also be prepared directly by hydrogenation of a compound of Formula IV in the presence of Raney nickel as shown in Example 5.

EXAMPLE 4

Ethyl 5-Amino-1,2-dihydro-3-phenylpyrido(3,4-b)pyrazin-7-ylcarbamate (I: $R_1=C_2H_5$; $R_2=H$; $R_3=H$; $R_4=H$)

A solution of ethyl 6-amino-5-nitro-4-[(2-oxophenyl-2-ethyl)amino]pyridin-2-ylcarbamate dioxanate (10:7) obtained in Example 2 (3.10 g., 7.25 mmoles) in ethyl alcohol (4 L.) was hydrogenated in the presence of Raney nickel (9 g., weighed wet after washing with ethyl alcohol) at atmospheric pressure with intermittent warming with a water bath. After six hours the catalyst was removed by filtration, and the filtrate was concentrated in vacuo (<40° C.) to 1/16 volume. The solid that deposited from the chilled mixture was collected by filtration and dried in vacuo over $P_2O_5$: yield, 1.82 g. From the filtrate a second crop was obtained: yield, 0.17 g. The total yield was 1.99 g. The properties are set forth in Table IV.

EXAMPLE 5

Hydrogenation of Ethyl 6-Amino-5-nitro-4-[[2-[4'-(trifluoromethyl)phenyl]-2-oxoethyl]-amino]pyridin-2-carbamate oxime A solution of the oxime (0.5 g.) in ethanol (1000 ml.) containing Raney nickel (1.5 g. wet, washed successively with $H_2O$ and ethanol) was hydrogenated at room temperature and atmospheric pressure for 7 hours. The catalyst was removed by filtration through Celite under nitrogen, and the filtrate was concentrated in vacuo to 1/20 volume to deposit ethyl 5-amino-1,2-dihydro-3-[4'-(trifluoromethyl)phenyl]pyrido[3,4-b]pyrazin-7-ylcarbamate. The product was collected by filtration, washed with ether, and dissolved in a mixture of ethanol (35 ml.) and 1 N HCl (15 ml.) with warming. After filtration through Celite, the filtrate was neutralized with 1 N NaOH and concentrated in vacuo to deposit the product: yield, 0.20 g. (47%). This material was identical by thin-layer chromatography with that prepared by hydrogenation of the corresponding ketone.

The compounds set forth in Table IV were prepared by the procedure of Example 4 or Example 5, as indicated in Table IV. The properties of these compounds are set forth in Table IV. The first column of Table IV sets forth the structure of the group

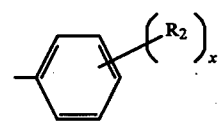

in the starting material, the formula for which appears in Table II or III (except as noted), and in the final product, the formula for which appears in Table IV.

TABLE IV

Ethyl 5-Amino-1,2-dihydro-3-phenyl-pyrido[3,4-b]pyrazin-7-ylcarbamates

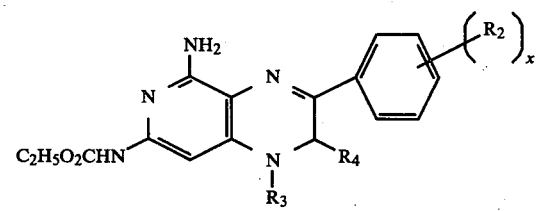

| Compound[a] | Procedure of Example | Reaction Time, Hours | Yield, % | M.p. °C. | Formula | Calcd, % C | Calcd, % H | Calcd, % N | Found, % C | Found, % H | Found, % N |
|---|---|---|---|---|---|---|---|---|---|---|---|
| $C_6H_5$ | 4 | 6 | 89 | >180 dec | $C_{16}H_{17}N_5O_2$ | 61.72 | 5.50 | 22.50 | 61.86 | 5.71 | 22.21 |
| 4-$CH_3C_6H_4$ | 4 | 5 | 83 | 270–80 dec | $C_{17}H_{19}N_5O_2$ | 62.75 | 5.89 | 21.52 | 62.96 | 6.13 | 21.31 |
| 2,4-$(CH_3)_2C_6H_3$ | 5 | 5 | 87 | 158–60 | $C_{18}H_{21}N_5O_2.0.1C_2H_6O.H_2O$ | 60.38 | 6.57 | 19.34 | 60.40 | 6.40 | 19.34 |
| 3,4-$(CH_3)_2C_6H_3$ | 4 | 5 | 83 | 190–2 dec | $C_{18}H_{21}N_5O_2.0.7C_2H_6O$ | 62.69 | 6.83 | 18.84 | 62.96 | 7.07 | 18.70 |
| 4-$FC_6H_4$ | 4 | 12 | 78 | 296–300 dec | $C_{16}H_{16}FN_5O_2$ | 58.35 | 4.90 | 21.27 | 58.42 | 4.90 | 21.38 |
| 2,4-$(Cl)_2C_6H_3$ | 5 | 24 | 64 | 203–5 dec | $C_{16}H_{15}Cl_2N_5O_2.0.8H_2O$ | 48.69 | 4.23 | 17.74 | 48.65 | 4.09 | 17.76 |
| 3,4-$(Cl)_2C_6H_3$ | 4 | 40 | 57 | 299–302 dec | $C_{16}H_{15}Cl_2N_5O_2.C_2H_6O.0.3HCl$ | 49.44 | 4.91 | 16.01 | 49.49 | 4.95 | 15.97 |
| 3-$CH_3OC_6H_4$ | 4 | 15 | 70 | 174–6 | $C_{17}H_{19}N_5O_3.0.3C_2H_6O.0.2H_2O$ | 58.92 | 5.96 | 19.52 | 59.11 | 6.32 | 19.62 |
| 4-$CH_3OC_6H_4$ | 4 | 6 | 71 | >170 dec | $C_{17}H_{19}N_5O_3.2.1H_2O.0.64C_2H_6O$ | 53.71 | 6.68 | 17.13 | 53.78 | 6.16 | 17.20 |
| 3,4,5-$(CH_3O)_3C_6H_2$ | 4 | 24 | 70 | 250–5 dec | $C_{19}H_{23}N_5O_5.HCl.0.5H_2O$ | 51.06 | 5.64 | 15.67 | 51.15 | 5.91 | 15.64 |
| 4-$H_2NC_6H_4$[b] | 4 | 6 | 17 | >300 dec | $C_{16}H_{18}N_6O_2.2.5HCl.0.5C_2H_6O$ | 46.35 | 5.38 | 19.08 | 46.71 | 5.27 | 19.33 |
| 4-$CF_3C_6H_4$ | 4 | 48 | 56 | >300 dec | $C_{17}H_{16}F_3N_5O_2.0.2H_2O.0.15HCl$ | 52.54 | 4.29 | 18.02 | 52.66 | 4.22 | 18.03 |
| 2-$C_{10}H_7$ | 4 | 6 | 61 | 251–6 dec | $C_{20}H_{19}N_5O_2.C_2H_6O.1.22HCl$ | 58.47 | 5.85 | 15.50 | 58.52 | 5.75 | 15.50 |
| $C_6H_5$, $R_4 = CH_3$ | 4 | 8 | 70 | 233–40 dec | $C_{17}H_{19}N_5O_2.0.43C_2H_6O.HCl.0.57H_2O$ | 54.74 | 6.10 | 17.87 | 54.76 | 6.33 | 17.87 |
| $C_6H_5$, $R_3 = CH_3$[c] | 4 | 3 | 39 | 173–5 dec | $C_{17}H_{19}N_5O_2.0.14C_2H_6O$ | 62.59 | 6.03 | 21.12 | 62.31 | 6.32 | 21.12 |

[a] $R_3$ and $R_4$ = H unless otherwise specified;
[b] corresponding group on starting material was 4-$O_2NC_6H_4$,
[c] starting material was compound VA wherein $R_1 = C_2H_5$; $R_2 = H$; and $R_3 = CH_3$ prepared as described in Example 3.

The 1,2-dihydropyrido[3,4-b]pyrazines of this invention are powerful inhibitors of the proliferation of cultured lymphoid leukemia L1210 cells as shown in Table V. The concentration causing a 50% inhibition of proliferation of the cells during 24 hours is similar to that observed for vincristine, vinblastine, and colchicine. Also, the addition to the test medium of inosine, thymidine, glycine, citrovorum factor, individually and in combinations, and elevated concentrations of amino acids and vitamins did not overcome the inhibitions.

In addition to cell cytotoxicity, the 1,2-dihydropyrido[3,4-b]pyrazines showed activity against lymphocytic leukemia P388 cells ($10^6$) implanted intraperitoneally in mice. Ethyl 5-amino-1,2-dihydro-3-phenylpyrido[3,4-b]pyrazin-7-ylcarbamate was also active in mice against P388 cells that were resistant to vincristine.

The 1,2-dihydropyrido[3,4-b]pyrazines at concentrations that prevented any increase in the cell number during a 24 hour period had little effect upon the synthesis of DNA, RNA, and protein by cultured L1210 cells during exposure for four hours. This result and those described above led to the determination of the effect of the 1,2-dihydropyrido[3,4-b]pyrazines upon cell division. Exposure of cultured L1210 cells to the 1,2-dihydropyrido[3,4-b]pyrazines inhibited cell division as measured by the mitotic index (MI) (Table V), which is the fraction of the cell population that is made up of metaphase cells. Subsequent experiments showed that these agents caused the accumulation in metaphase of human epidermoid carcinoma #2 cells, P388 cells, and P388 cells resistant to vincristine grown in suspension culture and of colon tumor #26 cells and colon tumor #38 cells grown on plastic surfaces. Further experiments showed that the 1-deaza-7,8-dihydropteridines of this invention possess antifungal activity against both human and plant pathogens. For example, 5-amino-1,2-dihydro-3-phenylpyrido[3,4-b]pyrazin-7-ylcarbamate was active against *Saccharomyces cerevisiae, Asperigillus niger, Penicillium italicum* and *Botrytis cinereae*.

Table V sets forth biological data for 1-deaza-7,8-dihydropteridines of this invention and for two prior art compounds. The first column of Table V sets forth the structure of the group

in the formula in the heading of the table for the 1-deaza-7,8-dihydropteridines tested.

TABLE V

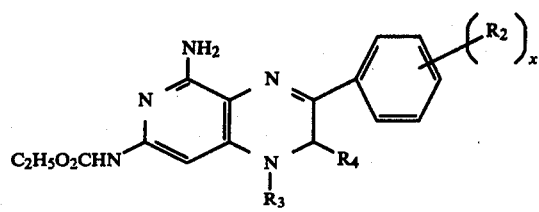

| Compound (a) | L1210 (b) ID$_{50}$ μM | Mitotic Index (c) 12h (μM) | 24h (μM) | P388 (d) 10$^6$ Tumor cell implant, i.p. Schedule, Days | % ILS (mg/kg) |
|---|---|---|---|---|---|
| Nocodazole | $27 \times 10^{-3}$ | | 0.19 (0.3) | | |
| Vincristine | $<1 \times 10^{-3}$ | | 0.62 (0.3) | 1 | 100 (2.7) (e) |
| | | | | 1,5,9 | 181 (1.3) (f) |
| | | | | 1–9 | 145 (0.33) (f) |
| C$_6$H$_5$ | $4.7 \times 10^{-3}$ (g) | 0.65 (0.03) | 0.54 (0.3) | 1 | 55 (12.5) (g) |
| | | | | 1 (h) | 50 (12) |
| | | | | 1,5,9 | 42 (4.5) |
| | | | | 1–9 | 51 (2) |
| 3-CH$_3$OC$_6$H$_4$ | $1.22 \times 10^{-3}$ | 0.56 (0.003) | | | |
| 4-CH$_3$OC$_6$H$_4$ | $4.1 \times 10^{-3}$ | | 0.27 (0.3) | 1 | 50 (25) |
| | | | | 1,5,9 | 63 (25) |
| | | | | 1–9 | 35 (3) |
| 3,4,5-(CH$_3$O)$_3$ C$_6$H$_2$ | $78 \times 10^{-10}$ | 0.41 (0.3) | | | |
| 4-H$_2$NC$_6$H$_4$ | $23 \times 10^{-3}$ (g) | | 0.19 (0.3) | 1 | 35 (50) |
| 4-FC$_6$H$_4$ | $6.8 \times 10^{-3}$ | 0.47 (0.01) | | 1–5 | 49 (3) |
| 2,4-Cl$_2$C$_6$H$_3$ | $44 \times 10^{-3}$ | | 0.20 (0.3) | 1–5 | 49 (12.5) |
| 3,4-Cl$_2$C$_6$H$_3$ | $18 \times 10^{-3}$ | 0.53 (0.03) 0.69 (0.01) | | 1–5 | 58 (10) |
| 4-CH$_3$C$_6$H$_4$ | $24 \times 10^{-3}$ | | 0.22 (0.3) | 1–5 | 30 (12) |
| 2,4-(CH$_3$)$_2$C$_6$H$_3$ | $42 \times 10^{-3}$ | 0.66 (0.1) | | 1–5 | 23 (20) (i) |
| 3,4-(CH$_3$)$_2$C$_6$H$_3$ | $138 \times 10^{-3}$ | | 0.16 (0.3) | 1–5 | 44 (12.5) |
| 4-CF$_3$C$_6$H$_4$ | $150 \times 10^{-3}$ | | 0.01 (0.3) | 1 | 0 (90) (i) |
| | | | | 1,5,9 | 0 (30) (i) |
| | | | | 1–9 | 17 (50) |
| 2-C$_{10}$H$_7$ | $6 \times 10^{-3}$ | 0.60 (0.03) | | 1–5 | 66 (10) (j), 53 (5) |
| C$_6$H$_5$, R$_4$ = CH$_3$ | $0.51 \times 10^{-3}$ | 0.69 (0.003) | | | |
| C$_6$H$_5$, R$_3$ = CH$_3$ | $160 \times 10^{-3}$ | 0.68 (0.3) | | 1 | 12 (100) |

(a) R$_3$ and R$_4$ = H unless otherwise specified.
(b) Concentration of agent that inhibits proliferation of cultured lymphoid leukemia L1210 cells to 50% control growth. Wheeler, G. P., Bowdon, B. J., Werline, J. A.; Adamson, D. J., and Temple, Jr., C., Cancer Res. 1982, 42, 0000.
(c) Fraction of the cell population of cultured lymphoid leukemia L1210 cells in mitoses [Ref. in b].
(d) Lymphocytic leukemia p388. Geran, R. I., Greenberg, N. H., MacDonald, M. M., Schulacker, A. M., Abott, B. J., Cancer Chemother. Rep., 1972, Part 3 (No. 2).
(e) Two 40th-day survivors.
(f) Three 40th-day survivors.
(g) Average of 2-determinations.
(h) Vincristine-resistant line of P388. Wilkoff, L. J. and Dulmadge, E. A., J. Natl. Cancer Inst., 1978, 61, 1521.
(i) Highest dose tested.
(j) One 30th-day survivor.

The data in Table V shows that the 1-deaza-7,8-dihydropteridines of this invention are active against leukemia in laboratory animals.

The compounds of the invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Also embraced within the purview of the present invention are therapeutic compositions of matter useful for ameliorating cancer diseases in mammals and containing the 1-deaza-7,8-dihydropteridines of this invention or pharmaceutically acceptable salts thereof.

The active ingredients of the therapeutic compositions and the novel compounds of the present invention inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

We claim:
1. A 1,2-dihydropyrido[3,4-b]pyrazine having the formula:

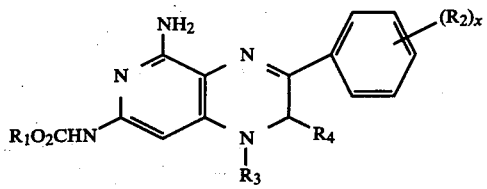

wherein x has a value of 1,2 or 3, $R_1$ is a lower alkyl group, $R_2$ is a member selected from the group consisting of hydrogen, alkyl radicals having from one to 12 carbon atoms, alkenyl radicals having from two to 15 carbon atoms, cycloalkyl radicals having from three to 20 carbon atoms, aralkyl and alkaryl radicals having from seven to 20 carbon atoms, a halogen radical, provided that when x has a value of 1 and $R_2$ is in the para position and $R_3$ and $R_4$ are both hydrogen, $R_2$ is not chlorine; hydroxyl, amino, alkoxy, aryloxy, carboxyl, alkylcarboxyl radicals having from one to 10 carbon atoms, alkylthio and arylthio radicals having from one to 20 carbon atoms, a sulfonic acid group, alkylsulfonyl and arylsulfonyl radicals having from one to 20 carbon atoms, alkylsulfinyl and arylsulfinyl radicals having from one to 20 carbon atoms, alkylamino and arylamino radicals having from one to 20 carbon atoms, and, when taken together with the aromatic ring to which it is attached, naphthyl; and $R_3$ and $R_4$ are either both hydrogen or one is hydrogen and the other is a lower alkyl group; and pharmaceutically acceptable salts thereof.

2. A compound as defined in claim 1 wherein $R_1$ is ethyl.
3. A compound as defined in claim 2 wherein $R_3$ and $R_4$ are each hydrogen and the group

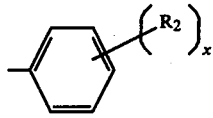

is selected from those having the following structures: $C_6H_5$, 4-$CH_3C_6H_4$, 2,4-$(CH_3)_2C_6H_3$, 3,4-$(CH_3)_2C_6H_3$, 4-$FC_6H_4$, 2,4-$(Cl)_2C_6H_3$, 3,4-$(Cl)_2C_6H_3$, 3-$CH_3OC_6H_4$, 4-$CH_3OC_6H_4$, 3,4,5-$(CH_3O)_3C_6H_2$, 4-$H_2NC_6H_4$, 4-$CF_3C_6H_4$ and 2-$C_{10}H_7$.

4. A compound as defined in claim 2 wherein $R_2$ and $R_4$ are each hydrogen and $R_3$ is methyl.
5. A compound as defined in claim 2 wherein $R_2$ and $R_3$ are each hydrogen and $R_4$ is methyl.
6. Ethyl 5-amino-1,2-dihydro-3-phenylpyrido[3,4-b]pyrazin-7-ylcarbamate.
7. Ethyl 5-amino-1,2-dihydro-3-(4-methoxyphenyl)-pyrido[3,4-b]pyrazin-7-ylcarbamate.
8. Ethyl 5-amino-1,2-dihydro-3-(3-methoxyphenyl)-pyrido[3,4-b]pyrazin-7-ylcarbamate.
9. Ethyl 5-amino-3-(4-fluorophenyl)-1,2-dihydropyrido[3,4-b]pyrazin-7-ylcarbamate.
10. Ethyl 5-amino-3-(2,4-dichlorophenyl)-1,2-dihydropyrido[3,4-b]pyrazin-7-ylcarbamate.
11. Ethyl 5-amino-1,2-dihydro-3-(2-naphthyl)-pyrido[3,4-b]pyrazin-7-ylcarbamate.
12. A pharmaceutical composition in dosage unit form comprising an amount of a compound as defined by claim 1 effective to treat fungal diseases in association with a pharmaceutical carrier.

* * * * *